United States Patent
Holton et al.

(10) Patent No.: US 6,548,293 B1
(45) Date of Patent: Apr. 15, 2003

(54) ENZYMATIC PROCESS FOR THE RESOLUTION OF ENANTIOMERIC MIXTURES OF β-LACTAMS

(75) Inventors: Robert A. Holton, Tallahassee, FL (US); Phong Vu, Little Falls, NJ (US)

(73) Assignee: FSU Research Foundation, Inc., Tallahassee, FL (US)

(*) Notice: Subject to any disclaimer, the term of this patent is extended or adjusted under 35 U.S.C. 154(b) by 4 days.

(21) Appl. No.: 09/688,852

(22) Filed: Oct. 16, 2000

Related U.S. Application Data

(60) Provisional application No. 60/160,103, filed on Oct. 18, 1999.

(51) Int. Cl.[7] .............................................. C12P 41/00
(52) U.S. Cl. ...................................................... 435/280
(58) Field of Search ......................................... 435/280

(56) References Cited

U.S. PATENT DOCUMENTS

| | | |
|---|---|---|
| 5,229,526 A | 7/1993 | Holton |
| 5,567,614 A | 10/1996 | Patel et al. |
| 5,811,292 A | 9/1998 | Patel et al. |
| 5,879,929 A | 3/1999 | Patel |

FOREIGN PATENT DOCUMENTS

| | | |
|---|---|---|
| EP | 0 552 041 B1 | 8/1993 |
| EP | 0 634 492 A1 | 7/1994 |
| WO | WO 99/41405 A1 | 8/1999 |

OTHER PUBLICATIONS

Basavaiah et al., "Enzymatic Resolution of trans–2–Arylcyclohexan–1–ols Using Crude Chicken Liver Esterase (CCLE) as Biocatalyst", *Tetrahedron: Asymmetry*, (1994), vol. 5, No. 2, pp. 223–234.

Brieva et al., "Chemoenzymatic Synthesis of the C–13 Side Chain of Taxol: Optically–Active 3–Hydroxy–4–phenyl β–Lactam Derivatives", *J. Org. Chem.*, (1993), vol. 58, pp. 1068–1075.

Gou et al., "A Practical Chemoenzymatic Synthesis of the Taxol C–13 SideChain N–Benzoyl–(2R, 3S)–3–phenylisoserine", *J. Org. Chem.*, (1993), vol. 58:5, pp. 1287–1289.

Greene T.W., "Protective Groups in Organic Synthesis", John Wiley & Sons, 2nd Edition (May 1991).

Liu, J.H., "Stereochemistry of the Michael addition of enolates to α–(sulfinyl)butenolides: An efficient partial synthesis of taxol", *J.H. Liu, Ph.D. Dissertation*, Florida State University (1991).

Mendoza et al. "Comparative Starch–gel Electrophoresis of Liver Esterases from Seven Species" Chemical Abstracts on STN, No. 75:84215.

Whitesell et al., Practical Enzymatic Resolution of Chiral Auxilaries—Enantiomerically Pure trans–2–Phenylcyelohexanol and trans–2–(α–Cumyl)cyclohexanol, *Chimia*, vol. 40 (1986), pp. 318–321.

International Search Report for PCT/US00/41204 dated Apr. 11, 2001.

*Primary Examiner*—Sandra E. Saucier
(74) *Attorney, Agent, or Firm*—Senniger, Powers, Leavitt & Roedel

(57) ABSTRACT

A process for the resolution of an enantiomeric mixture of β-lactams containing an ester, the process comprising selectively hydrolyzing the ester of one of the enantiomers by combining the mixture with homogenized liver.

38 Claims, No Drawings

ENZYMATIC PROCESS FOR THE RESOLUTION OF ENANTIOMERIC MIXTURES OF β-LACTAMS

CROSS-REFERENCE TO RELATED APPLICATIONS

This application claims the benefit of U.S. Provisional Application No. 60/160,103 filed Oct. 18, 1999.

BACKGROUND OF THE INVENTION

The present invention relates to enzymatic processes for the resolution of enantiomeric mixtures of β-lactams useful in the preparation of taxanes.

The taxane family of terpenes, of which taxol and docetaxel are members, has attracted considerable interest in both the biological and chemical arts. Such taxanes may be prepared through a variety of semi-synthetic routes. In one, a β-lactam is coupled to a derivative of 10-deacetylbaccatin III to form a sidechain at the C-13 position of the derivative. As the stereochemistry of these taxanes may affect their pharmaceutical activity, methods allowing efficient stereospecific preparation of the intermediate β-lactam, as well as the final taxane products, have been the subject of investigation.

Brieva et al. (Brieva, R.; Crich, J. Z. and Sih, C. J., *J. Org. Chem.* 1993,58, 1068) reported that racemic β-lactam underwent selective kinetic hydrolysis with several Pseudomonas lipases and two penicillinases. Pseudomonas lipases used by Brieva et al. include P-30, AK and K-10.

Similarly, Patel reported in U.S. Pat. No. 5,879,929, that enantiomeric mixtures of certain β-lactams and, in particular, racemic mixtures of certain β-lactams, can be resolved by a stereoselective hydrolysis using a variety of lipases and enzymes. Lipases identified by Patel include Amano PS-30 (*Pseudomonas cepacia*), Amano GC-20 (*Geotrichum candidum*), Amano APF (*Aspergillus niger*), Amano AK (Pseudomonas sp.), *Pseudomonas fluorescens* lipase (Biocatalyst Ltd.), Amano Lipase P-30 (Pseudomonas sp.), Amano P (*Pseudomonas fluorescens*), Amano AY-30 (*Candida cylindracea*), Amano N (*Rhizopus niveus*), Amano R (Penicillium sp.), Amano FAP (*Rhizopus oryzae*), Amano AP-12 (*Aspergillus niger*), Amano MAP (*Mucor meihei*), Amano GC-4 (*Geotrichum candidum*), Sigma L-0382 and L-3126 (porcine pancreas), Lipase OF (Sepracor), Esterase 30,000 (Gist-Brocarde), KID Lipase (Gist-Brocarde), Lipase R (Rhizopus sp., Amano), Sigma L-3001 (Wheat germ), Sigma L-1754 (*Candida cylindracea*), Sigma L-0763 (*Chromobacterium viscosum*) and Amano K-30 (*Aspergillus niger*). Enzymes identified by Patel include enzymes derived from animal tissue such as esterase from pig liver, α-chymotrypsin and pancreatin from pancreas such as Porcine Pancreatic Lipase (Sigma). While these enzymes may be used in the stereoselective hydrolysis of β-lactams, the required purification of the enzyme can significantly increase the cost of the preparation of the β-lactam.

Whitesell et al. (Whitesell, J. K. Lawrence, R. M. *Chimia*, 1986, 40, 315) and Basavaiah et al. (Basavaiah,, D. and Rao, P. *Tetrahedron. Asym.*, 1994, 5, 223–234) reported successful application of pig liver acetone powder (PLAP), bovine liver acetone powder (BLAP) and chicken liver acetone powder (CLAP), in the resolution of numerous chiral secondary alcohols. Experimental evidence obtained to date, however, suggests that the use of these materials results in a product having relatively low optical purity. While the reason for this is not entirely clear, it is believed that this is the result of incomplete reaction rather than the enzyme's lack of selectivity which, in turn, is likely a consequence of inconsistent amounts of active enzyme present in different batches of the liver acetone powder.

SUMMARY OF THE INVENTION

Among the objects of the present invention, therefore, is the provision of enzymatic processes for the resolution of enantiomeric mixtures of β-lactams useful in the preparation of taxanes which offers improved reproducibility as compared to processes which employ acetone powders of animal livers and which compares favorably in cost to processes which employ purified lipases and other enzymes.

Briefly, therefore, the present invention is directed to a process for the resolution of a racemic mixture of β-lactams which contain an ester. The process comprises selectively hydrolyzing the ester of one of the enantiomers by combining the mixture with homogenized liver.

Other objects and features of this invention will be in part apparent and in part pointed out hereinafter.

DETAILED DESCRIPTION OF THE PREFERRED EMBODIMENTS

A. Starting Materials

In general, the β-lactam enantiomers in the mixture have the following structural formula:

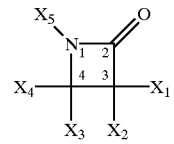

wherein $X_1$ is —$OX_6$;

$X_2$ is hydrogen, hydrocarbyl, substituted hydrocarbyl, or heterocyclo;

$X_3$ is hydrogen, hydrocarbyl, substituted hydrocarbyl, or heterocyclo;

$X_4$ is hydrocarbyl, substituted hydrocarbyl, or heterocyclo;

$X_5$ is hydrogen, hydrocarbyl, substituted hydrocarbyl, —$COX_{10}$, —$COOX_{10}$, or —$CONX_8X_{10}$;

$X_6$ is acyl;

$X_8$ is hydrogen, hydrocarbyl, substituted hydrocarbyl, or heterocyclo; and $X_{10}$ is hydrocarbyl, substituted hydrocarbyl, or heterocyclo.

Preferably, $X_2$ and $X_3$ are hydrogen and the mixture contains the 3S,4R and 3R,4S enantiomers, and more preferably a racemic mixture of these enantiomers. Still more preferably, $X_2$ and $X_3$ are hydrogen; $X_5$ is hydrogen, hydrocarbyl, substituted hydrocarbyl, —$COX_{10}$, or —$COOX_{10}$; $X_{10}$ is alkyl, aryl or heterocyclo; and the mixture contains the 3S,4R and 3R,4S enantiomers, preferably a racemic mixture of these enantiomers. In a particularly preferred embodiment, $X_2$ and $X_3$ are hydrogen; $X_5$ is hydrogen, hydrocarbyl, substituted hydrocarbyl, —$COX_{10}$, or —$COOX_{10}$; $X_{10}$ is alkyl, aryl or heterocyclo; $X_4$ is 2-furyl, 3-furyl, 2-pyridyl, 3-pyridyl, 4-pyridyl, 2-thienyl, 3-thienyl, substituted phenyl (substituted with any of the substituents identified elsewhere herein as hydrocarbyl substituents such as halo or nitro with the phenyl being mono or poly substituted in one or more of the ortho, meta or para positions), cycloalkyl, or alkenyl, and the mixture contains the 3S,4R and 3R,4S enantiomers, preferably a racemic mixture of these enantiomers.

Enantiomeric mixtures of the β-lactam starting materials may be obtained as described in Example 1 herein, or by methods analogous to those described in U.S. Pat. No. 5,229,526 which is incorporated herein by reference.

Homogenates of fresh or fresh frozen crude liver may be prepared using a high speed blender or other grinder. The liver is ground into pieces of a relatively small size and suspended in an aqueous solution. Preferably, about 1 pound (about 450 grams) of liver is combined with sufficient liquid to form about 0.5 to about 2 liters of homogenate, more preferably about 0.75 to about 1.25 liters, and most preferably about 1 liter of homogenate. In a preferred embodiment, the homogenate is buffered, preferably to a pH of about 8 with a phosphate or other suitable buffering agent.

Derivatives of homogenates are also included within the invention, such as refined fractions. To obtain refined fractions one may subject the homogenate to a series of fractionation procedures, the number of fractionation steps employed being dependent on the degree of purification desired. The series of fractionation steps could involve column chromatography such as a gel filtration column, centrifugation, heat treatment, precipitation, filtration or various other appropriate means of purification.

In general, the liver may be obtained from any animal. Preferably, the liver is avian or mammalian, more preferably chicken, turkey, pig or beef, and most preferably beef.

Stereoselective Hydrolysis

In general, a solution of β-lactam mixture in an organic solvent is combined with the homogenate to form a reaction mixture which contains about 1 gram of β-lactam to about 5 ml. to about 100 ml. of homogenate, more preferably about 1 gram of β-lactam to about 50 ml. of homogenate (with the homogenate containing about 450 grams of liver and sufficient liquid to form about 1 liter of homogenate). The reaction mixture is preferably adjusted to and maintained at about pH 7 to pH 8, preferably with a buffer, more preferably with a phosphate buffer.

The hydrolysis is preferably conducted in an aqueous, such as a buffered aqueous (e.g., phosphate buffer), medium or in an aqueous medium containing a miscible or immiscible organic solvent. For example, the reaction may be conducted in a biphasic solvent system comprising an organic phase, immiscible in water, and an aqueous phase.

Solvents for the organic phase of a biphasic solvent system may be any organic solvent immiscible in water, such as toluene, benzene, hexane, cyclohexane, xylene, trichlorotrifluoroethane, dichloromethane, ether and the like, and is preferably ether or toluene. Typically, the concentration of the β-lactam mixture will be about 0.1 to about 1 millimolar. The aqueous phase is water, preferably deionized water, or a suitable aqueous buffer solution, especially a phosphate buffer solution. The biphasic solvent system preferably comprises between about 10 to 90 percent by volume of organic phase and between about 90 to 10 percent by volume of aqueous phase.

The reaction time may be selected based on the homogenate, the temperature and the enzyme concentration. Temperatures of from about 4° C. to about 60° C. are preferably employed.

Separation

The products of the stereoselective conversions may be isolated and purified by methodologies such as extraction, distillation, crystallization, column chromatography, and the like.

Definitions

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Preferably, these moieties comprise 1 to 20 carbon atoms.

The "substituted hydrocarbyl" moieties described herein are hydrocarbyl moieties which are substituted with at least one atom other than carbon, including moieties in which a carbon chain atom is substituted with a hetero atom such as nitrogen, oxygen, silicon, phosphorous, boron, sulfur, or a halogen atom. These substituents include halogen, heterocyclo, alkoxy, alkenoxy, alkynoxy, aryloxy, hydroxy, protected hydroxy, keto, acyl, acyloxy; nitro, amino, amido, nitro, cyano, and thiol.

The alkyl groups described herein are preferably lower alkyl containing from one to six carbon atoms in the principal chain and up to 20 carbon atoms. They may be straight or branched chain and include methyl, ethyl, propyl, isopropyl, butyl, hexyl and the like.

The alkenyl groups described herein are preferably lower alkenyl containing from two to six carbon atoms in the principal chain and up to 20 carbon atoms. They may be straight or branched chain and include ethenyl, propenyl, isopropenyl, butenyl, isobutenyl, hexenyl, and the like.

The alkynyl groups described herein are preferably lower alkynyl containing from two to six carbon atoms in the principal chain and up to 20 carbon atoms. They may be straight or branched chain and include ethynyl, propynyl, butynyl, isobutynyl, hexynyl, and the like.

The terms "aryl" or "ar" as used herein alone or as part of another group denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl and substituted phenyl are the more preferred aryl.

The terms "halogen" or "halo" as used herein alone or as part of another group refer to chlorine, bromine, fluorine, and iodine.

The terms "heterocyclo" or "heterocyclic" as used herein alone or as part of another group denote optionally substituted, fully saturated or unsaturated, monocyclic or bicyclic, aromatic or nonaromatic hydrocarbon groups having at least one heteroatom in at least one ring, and preferably 5 or 6 atoms in each ring. The heterocyclo group preferably has 1 or 2 oxygen atoms, 1 or 2 sulfur atoms, and/or 1 to 4 nitrogen atoms in the ring, and may be bonded to the remainder of the molecule through a carbon or heteroatom. Exemplary heterocyclo include furyl, thienyl, pyridyl and the like. Exemplary substituents include one or more of the following groups: hydrocarbyl, substituted hydrocarbyl, keto, hydroxy, protected hydroxy, acyl, acyloxy, alkoxy, alkenoxy, alkynoxy, aryloxy, halogen, amido, amino, nitro, cyano, and thiol.

The acyl moieties described herein contain hydrocarbyl, substituted hydrocarbyl or heterocyclo moieties.

The term "stereoselective conversion," as used herein, refers to the preferential reaction of one enantiomer relative to another, that is, asymmetric, enantioselective, reaction. Likewise, the terms "stereoselective hydrolysis", refers to the preferential hydrolysis of one enantiomer relative to another.

The term "mixture," as said term is used herein in relation to enantiomeric compounds, denotes mixtures having equal (racemic) or non-equal amounts of enantiomers.

The term "resolution" as used herein denotes partial, as well as, preferably, complete resolution.

The terms "hydroxyl protecting group" and "hydroxy protecting group" as used herein denote a group capable of protecting a free hydroxyl group ("protected hydroxyl") which, subsequent to the reaction for which protection is employed, may be removed without disturbing the remainder of the molecule. A variety of protecting groups for the hydroxyl group and the synthesis thereof may be found in "Protective Groups in Organic Synthesis" by T. W. Greene, John Wiley and Sons, 1981, or Fieser & Fieser. Exemplary hydroxyl protecting groups include methoxymethyl, 1-ethoxyethyl, benzyloxymethyl, (.beta.-trimethylsilylethoxy)methyl, tetrahydropyranyl, 2,2,2-trichloroethoxycarbonyl, t-butyl(diphenyl)silyl, trialkylsilyl, trichloromethoxycarbonyl and 2,2,2-trichloroethoxymethyl.

EXAMPLES

Example 1

Beef Liver Resolution of N-PMP-4-(2-furyl)-β-lactam

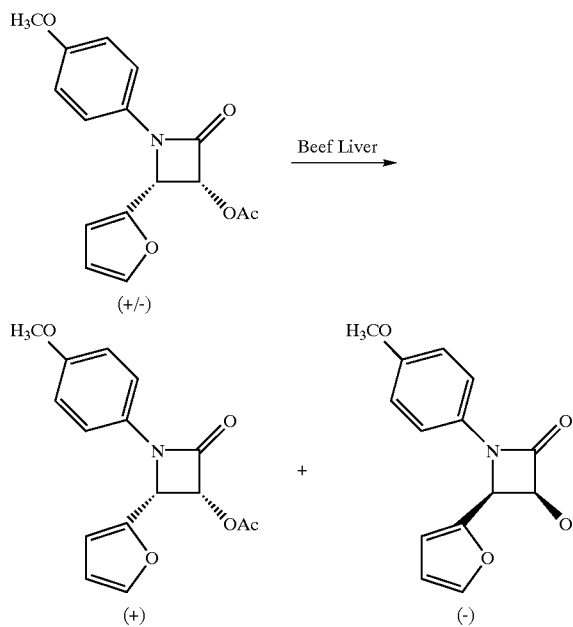

To a 4-L Erlenmeyer flask equipped with a mechanical stirrer was added a solution of 62 g (0.205 mol) of recrystallized racemic β-lactam in 1.0 L of toluene. The solid was completely dissolved by warming with a 40° C. water bath and then cooling to ambient temperature. To a 1-L graduated cylinder was added 87.1 g (0.5 mol) of $K_2HPO_4$, and 4.9 g (0.036 mol) of $KH_2PO_4$ diluted to the 1000 mL mark with RO water and mixed to dissolve completely. A beef liver suspension was prepared by adding 20 g of frozen beef liver (Premium Select Brand, Nebraskaland, Inc., New York) to a blender and then adding the pH 8 buffer to make a total volume of 1 L. The mixture was blended to make a homogeneous suspension which was then added directly to the toluene solution. The mixture was stirred for 22 h at ambient temperature. The layers were separated and the aqueous layer was extracted with 1 L of ethyl acetate. The organic layers were combined and concentrated to give 67 g of white powder. The powder was recrystallized from 600 mL of hot absolute ethanol to give 23.4 g (0.078 mol, 38%) of optically pure β-lactam (+)– m.p. 153–155° C.; $[\alpha]^{20}_{589}$=+38.1° (MeOH, c=0.7).

Example 2

As noted previously, others have reported successful application of pig liver acetone powder (PLAP), bovine liver acetone powder (BLAP) and chicken liver acetone powder (CLAP), in the resolution of numerous chiral secondary alcohols. The application of a BLAP biphasic enzymatic resolution procedure to (±)-1a resulted in 37% yield of the hydroxy β-lactam (–)-2a and a 33% yield of the acetoxy β-lactam (–)-1a after 3 h at room temperature (Scheme 1).

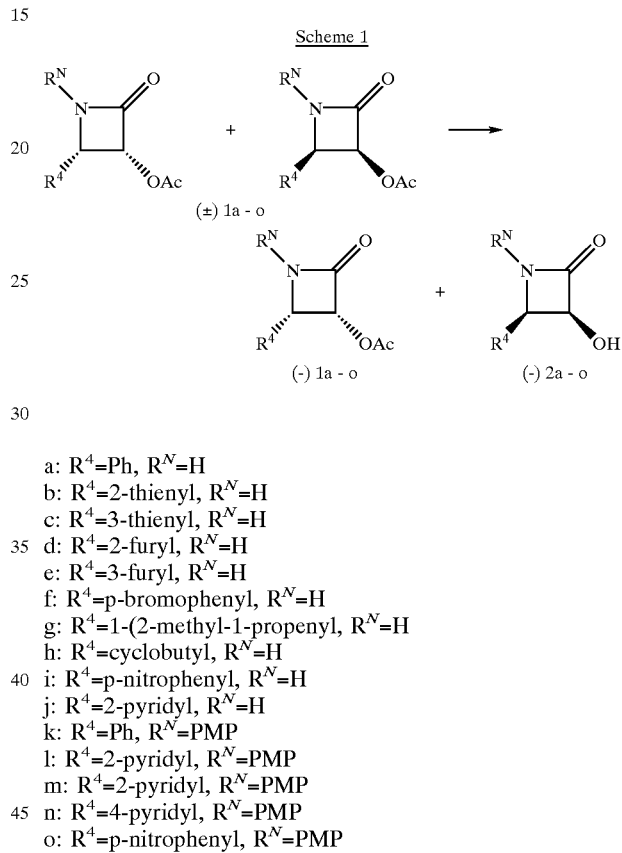

a: $R^4$=Ph, $R^N$=H
b: $R^4$=2-thienyl, $R^N$=H
c: $R^4$=3-thienyl, $R^N$=H
d: $R^4$=2-furyl, $R^N$=H
e: $R^4$=3-furyl, $R^N$=H
f: $R^4$=p-bromophenyl, $R^N$=H
g: $R^4$=1-(2-methyl-1-propenyl), $R^N$=H
h: $R^4$=cyclobutyl, $R^N$=H
i: $R^4$=p-nitrophenyl, $R^N$=H
j: $R^4$=2-pyridyl, $R^N$=H
k: $R^4$=Ph, $R^N$=PMP
l: $R^4$=2-pyridyl, $R^N$=PMP
m: $R^4$=2-pyridyl, $R^N$=PMP
n: $R^4$=4-pyridyl, $R^N$=PMP
o: $R^4$=p-nitrophenyl, $R^N$=PMP The hydroxy β-lactam (–)-2a was shown to be optically pure by comparison to the reported specific rotation and by $^1H$ NMR studies on its Mosher ester as well as Eu(hfc)$_3$ chemical shift analysis on the alcohol. The optical purity of recovered acetate (–)-1a varied from 76%ee to >95%ee, and was found to be dependent upon the batch of liver acetone powder used. Conversion of acetate (–)-1a to the desired hydroxy β-lactam (+)-2a was carried out using Liu's pyrolidine-pyridine procedure. Liu, J. H., Ph.D. Dissertation, The Florida State University, 1991. Thus, liver acetone powder is highly selective toward the 3S enantiomer of β-lactam. This selectivity was further confirmed by the fact that the optically pure (–)-3R,4S-β-lactam 1a was not hydrolyzed under the same conditions after 24 h. Therefore, the low optical purity of the recovered (–)-1a is the result of incomplete reaction rather than the enzyme's lack of selectivity. This is probably a consequence of inconsistent amounts of active enzyme present in different batches of the liver acetone powder. It was reasoned that this inconsistency could be eliminated if the enzyme was not subjected to the drying process in the acetone powder preparation.

Hence, a phosphate buffered beef liver solution (BBLS) was prepared by homogenizing 1 lb of frozen beef liver in a 0.5 M $KH_2PO_4/K_2HPO_4$ pH 8 buffer to make 1 L of total solution. A 50 mL aliquot of this BBLS was found to selectively hydrolyze the (+)-1a isomer from 1.0 g of (±)-1a in 15 minutes, leaving the (−)-1a isomer unchanged. The enantiomeric excess of both the acetate and the alcohol was found to be essentially 100% as determined by the methods described previously.

Similarly, buffered chicken (BCLS), pig (BPLS), and turkey (BTLS) liver solutions showed the same activity toward (±)-1a. Table I summarizes the enzyme sources used in the resolution and their efficiencies.

TABLE I

Efficacies of Various Enzyme Sources in the Resolution of (±)-1a

| Enzyme Source | (−)-1a | | | (−)-2a | | | Time (hrs) |
|---|---|---|---|---|---|---|---|
| | Yield (%) | $\alpha_{578}25$ $CHCL_3$ | % ee | Yield (%) | $\alpha_{578}25$ $CHCL_3$ | % ee | |
| BLAP | 33 | −40.0 | 78 | 37 | −178.6 | >95 | 3.0 |
| BBLS | 48 | −46.9 | >95 | 45 | −178.7 | >95 | 0.25 |
| BCLS | 53 | −40.0 | 78 | 45 | −175.6 | >95 | 0.25 |

TABLE I-continued

Efficacies of Various Enzyme Sources in the Resolution of (±)-1a

| Enzyme Source | (−)-1a | | | (−)-2a | | | Time (hrs) |
|---|---|---|---|---|---|---|---|
| | Yield (%) | $\alpha_{578}25$ $CHCL_3$ | % ee | Yield (%) | $\alpha_{578}25$ $CHCL_3$ | % ee | |
| BTLS | 55 | −40.5 | 78 | 31 | −179.4 | >95 | 0.25 |
| BPLS | 62 | −30.8 | 65 | 36 | −175.8 | >95 | 0.25 |

It is unclear which enzyme in the liver is responsible for this enantioselective lipase activity. Undoubtedly, there is more than one active enzyme in a crude solution of beef liver. Nevertheless, this enzymatic methodology was found to be ideally suited for the preparation of other optically active β-lactam analogs. Table II shows a variety of β-lactam substrates which were resolved by BBLS. As indicated in the table, the BBLS enzymatic resolution procedure proved effective for almost all of the substrates examined. Problems did arise in the hydrolysis of substrates containing highly polar groups. For example, when $R^4$=p-nitrophenyl and $R^N$=H, the resulting alcohol was not isolable. Similar problems were also encountered with substrates where $R^4$=pyridyl. It is unclear whether the product was lost to the aqueous layer in these reactions or underwent decomposition during the course of the reaction.

To remedy this problem, the $R^N$ group was changed to the more hydrophobic p-methoxyphenyl (PMP) group. As can be seen from Table II, introduction of the PMP group increased the time required for the complete hydrolysis of the 3S,4R enantiomer. This is probably due to the loss of a hydrogen bonding site in addition to the increase in steric bulk. Nonetheless, this allowed the alcohol product to be isolated and characterized. Interestingly, it was found that the hydrolyzed products from the substrates having $R^4$=2-pyridyl, 4-pyridyl and 4-nitrophenyl were a mixture of cis and trans hydroxy β-lactams.

Currently, this enzymatic resolution procedure is the most general and convenient protocol for the production of various optically active β-lactams suitable for the preparation of taxol C13 side chain analogs.

TABLE II

BBLS Resolution of Various β-lactams (±)-1a-o

| 1 | $R^4$ | $R^N$ | Time (h) | Acetate | | | Alcohol | | |
|---|---|---|---|---|---|---|---|---|---|
| | | | | yield (%) | $\alpha_{578}25$ $CHCL_3$ | % ee | yield (%) | $\alpha_{578}25$ $CHCL_3$ | % ee |
| a | Phenyl | H | 0.25 | 46 | −46 | >95 | 45 | −175 | >95 |
| b | 2-Thienyl | H | 0.25 | 42 | −93 | >95 | 49 | −135 | >95 |
| c | 3-Thienyl | H | 2 | 49 | −82 | >95 | 25 | −119 | >95 |
| d | 2-furyl | H | 0.25 | 40 | −125 | >95 | 40 | −107 | >95 |
| e | 3-furyl | H | 1.2 | 43 | −91 | >95 | 38 | −86 | >95 |
| f | p-Bromo-phenyl | H | 0.25 | 54 | −36 | 71 | 39 | −122 | >95 |
| g | 1-(2-methyl-1-propenyl) | H | 4 | 45 | −23 | >95 | 33 | −100 | >95 |
| h | Cyclobutyl | H | 1 | 40 | −79 | >95 | 49 | −29 | >95 |
| i | p-Nitrophenyl | H | 1 | 38 | −49 | 90 | 0 | — | — |
| j | 2-Pyridyl | H | 0.5 | 45 | −5 | >95 | 0 | — | — |
| k | Phenyl | PMP | 24 | 42 | +8 | >95 | 45 | −172 | >95 |
| l | 2-Pyridyl | PMP | 16 | 42 | +42 | >95 | 30 | Mixture of cis + trans | |
| m | 3-Pyridyl | PMP | 10 | 33 | +8.7 | >95 | 45 | | |
| n | 4-Pyridyl | PMP | 10 | 55 | +25 | 75 | 43 | | |
| o | p-Nitrophenyl | PMP | 24 | 35 | +48 | >95 | 14 | | |

Materials and Methods

Frozen livers were bought from a local grocery store. Beef liver was packed by Fremont Beef Company, Fremont, Nebr. 68025.

General Procedure for Preparation of Liver Acetone Powder. Beef Liver Acetone Powder (BLAP).

Frozen beef liver (250 g) was homogenized with a blender, and 200 mL of acetone was added. The precipitate was collected by filtration through coarse filter paper and dried under high vacuum for 2 h. The dried mass was further powderized with a blender to give 78 g BLAP and was stored at −30° C.

General Procedure for Liver Acetone Powder Mediated Hydrolysis. β-Lactam (−)-1a.

To a solution of 1.0 g (4.87 mmol) of (±)-1a in 10 mL of diethyl ether at 25° C. was added 40 mL of 0.5 M phosphate buffer and 1.0 g of BLAP. After 3 h, 100 mL of brine was added. After 10 min, the mixture was diluted with 200 mL of ethyl acetate. The organic layer was separated, washed with brine and dried over $Na_2SO_4$ and concentrated. Flash chromatography eluting with 75% ethyl acetate in hexanes gave 0.33 g (1.6 mmol) of (−)-1a as the less polar fraction and 0.29 g (1.8 mmol) of (−)-2a as the polar fraction.

General Procedure for Phosphate Buffer Liver Solution. Buffered Beef Liver Solution (BBLS).

Frozen beef liver (500 g) was homogenized with a blender. The mixture was diluted to 1 L of volume with pH 8 (~0.5 M of $PO_4^{-2}$) phosphate buffer and stored at −30° C. (no loss of enzyme activity after 15 days).

General Procedure for Buffered Liver Solution Mediated Hydrolysis. β-Lactam (−)-1a.

To a solution of 1.0 g (4.87 mmol) of (±)-1a in 100 mL of diethyl ether at 25° C. was added 50 mL of the BBLS and 50 mL of phosphate buffer (0.5 M, pH 8). After 15 min, 10 mL of brine was added. The reaction mixture was diluted with 200 mL of acetone, filtered and concentrated. The residue was diluted with 200 mL of ethyl acetate, washed with brine, dried over $Na_2SO_4$ and concentrated to give a yellow solid. Flash chromatography eluting with 75% ethyl acetate in hexane gave 0.480 g (2.34 mmol, 48%) of (−)-1a as the less polar fraction and 0.354 g (2.17 mmol, 45%) of (−)-2a as the polar fraction.

1a: mp 187–189° C.; $[\alpha]_{578}^{25}$=−46° (c=1.0, $CHCl_3$); >95% ee; $^1$H NMR (300 MHZ, $CDCl_3$) δ (ppm): 1.67 (s, 3H), 5.04 (d, J=4.5 Hz, 1H), 5.89 (dd, J=4.5, 2.8 Hz, 1H), 6.22 (bm, 1H), 7.34 (m, 5H).

2a: mp 190–192° C.; $[\alpha]_{578}^{25}$=−175° (c=1.0, MeOH); >95% ee; $^1$H NMR (300 MHZ, $CDCl_3$) δ (ppm): 1.95 (d, J=9.9 Hz, 1H), 4.96 (d, J=4.6 Hz, 1H), 5.12 (m. 1H), 6.15 (bm, 1H), 7.41 (m, 5H).

β-Lactam (−)-1b.

Following the general procedure, 0.57 g (0.65 mmol) of (±)-1b was treated with BBLS for 0.25 h to give 0.225 g (0.14 mmol, 30%) (−)-1b.

(−)-1b: mp 135–136° C.; $[\alpha]_{578}^{25}$=−93° (c=1.0, $CHCl_3$); $^1$H NMR (300 MHZ, $CDCl_3$) δ (ppm): 1.84 (s, 3H), 5.28 (d, J=4.6 Hz, 1H), 5.87 (dd, J=4.6, 2.7 Hz, 1H), 6.55 (bm, 1H), 7.02 (m, 2H), 7.33 (dd, J=4.6, 1.7 Hz, 1H).

2b: mp 144–145° C.; $[\alpha]_{578}^{25}$=−135° (c=1.0, MeOH); >95% ee; $^1$H NMR (300 MHZ, $CDCl_3$) δ (ppm): 2.55 (d, J=9.7 Hz, 1H), 5.1 (m, 1H), 5.17 (d, J=5.0 Hz, 1H), 6.33 (bm, 1H), 7.10 (m, 2H), 7.37 (dd, 4.5, 1.3 Hz, 1H).

β-Lactam (−)-1d.

Following the general procedure, 0.57 g (2.92 mmol) of (±)-1d was treated with BBLS for 0.25 h to give 0.225 g (1.15 mmol, 40%) of (−)-1d and 0.16 g (1.04 mmol, 35%) of (−)-2d.

(−)-1d: mp 158–159° C.; $[\alpha]_{578}^{25}$=−134° (c=1.1, $CHCl_3$); >95% ee; $^1$H NMR (300 MHZ, $CDCl_3$) δ (ppm): 1.90 (s, 3H), 5.04 (d, J=5.0 Hz, 1H), 5.89 (d, J=5.0, 2.0 Hz, 1H), 6.20 (bm, 1H), 6.40 (bm, 2H), 7.44 (s, 1H)

2d: mp 144–145° C.; $[\alpha]_{578}^{25}$=−107° (c=1.0, MeOH); >95% ee; $^1$H NMR (300 MHZ, $CDCl_3$) δ (ppm): 2.78 (bm, 1H), 3.49 (d, J=5.0 Hz, 1H), 4.91 (d, J=5.0 Hz, 1H), 5.12 (bm, 1H), 6.13 (bm, 1H), 6.45 (m, 2H), 7.49 (d, J=1.2 Hz, 1H)

β-Lactam (−)-1i.

Following the general procedure, 0.1 g (0.4 mmol) of (±)1i was treated with BBLS for 1 h to give 0.030 g (0.14 mmol, 30%) (−)-1i.

(−)-1i: mp 198–199° C.; $[\alpha]_{578}^{25}$=−49° (c=1.0, $CHCl_3$); 90% ee; $^1$H NMR (300 MHZ, $CDCl_3$) δ (ppm): 1.73 (s, 3H), 5.16 (d, J=4.7 Hz, 1H), 5.95 (dd, J=4.7, 3.1 Hz, 1H), 6.58 (bm, 1H), 7.52 (d, J=8.5 Hz, 2H), 8.24 (d, J=8.5 Hz, 2H)

β-Lactam (−)-1j.

Following the general procedure, 1.0 g of (±)-1j was treated with BBLS for 24 h to give 0.223 g of (−)-1j.

(−)-1j: mp 99–100° C.; $[\alpha]_{578}^{25}$=−5° (c=1.0, $CHCl_3$); >95% ee; $^1$H NMR (300 MHZ, $CDCl_3$) δ (ppm): 1.74 (s, 3H), 5.15 (d, J=5.1 Hz, 1H), 6.06 (dd, J=5.1, 2.3 Hz, 1H), 6.46 (bm, 1H), 7.26 (m, 1H), 7.36 (d, J=7.8 Hz, 1H), 7.73 (ddd, J=8.5, 7.4, 2.1 Hz, 1H), 8.61 (d, J=4.9 Hz, 1H).

β-Lactam (−)-1k.

Following the general procedure, 1.0 g (3.21 mmol) of (±)-1k was treated with BBLS for 24 h to give 0.42 g (1.35 mmol, 42%) of (+)-1k and 0.377g (01.44 mmol, 45%) of (−)-2k.

(+)-1k: mp 164–165° C.; $[\alpha]_{578}^{25}$=+8° (c=1.0, $CHCl_3$); >95% ee; $^1$H NMR (300 MHZ, $CDCl_3$) δ (ppm): 1.67 (s, 3H), 3.75 (s, 3H), 5.34 (d, J=5.0 Hz, 1H), 5.94 (d, J=5.0 Hz, 1H), 6.81 (d, J=8.4 Hz, 2H), 7.31 (m, 7H)

β-Lactam 1l: mp 154–155° C.; $[\alpha]_{578}^{25}$=+42° (c=1.0, $CHCl_3$); >95% ee; $^1$H NMR (300 MHZ, $CDCl_3$) δ (ppm): 1.74 (s, 3H), 3.76 (s, 3H), 5.48 (d, J=5.3 Hz, 1H), 6.12 (d, j=5.3 Hz, 1H), 6.81 (d, J=9.1 Hz, 2H), 7.29 (m, 4H), 7.68 (ddd, J=7.7, 7.8, 1.7, Hz, 1H), 8.64 (d, J=4.7 Hz, 1H);

β-Lactam 1m: mp 158–160° C.; $[\alpha]_{578}^{25}$=+8.7° (c=1.0, $CHCl_3$); >95% ee; $^1$H NMR (300 MHZ, $CDCl_3$) δ (ppm): 1.74 (s, 3H), 3.76 (s,3H), 5.38 (d, J=4.5 Hz, 1H), 5.98 (d, J=4.5 Hz, 1H), 6.81 (d, J=9.1 Hz, 2H), 7.25 (d, J=9.1 Hz, 2H), 7.30 (m, 1H), 7.64 (m, 1H), 8.61 (m, 2H).

β-Lactam 1n: mp 158–159° C.; $[\alpha]_{578}^{25}$=+25° (c=1.0, $CHCl_3$); >95% ee; $^1$H NMR (300 MHZ, $CDCl_3$) δ (ppm): 1.74 (s, 3H), 3.76 (s, 3H), 5.32 (d, J=5.0 Hz, 1H), 5.98 (d, J=5.0 Hz, 1H), 6.83 (d, J=9.1 Hz, 2H), 7.23 (m, 4H), 8.62 (m, 2H);

β-Lactam 2n-trans: $^1$H NMR (300 MHZ, $CDCl_3$) δ (ppm): 3.75 (s, 3H), 4.70 (s, 1H), 4.84 (s, 1H), 6.79 (m, 2H), 7.16 (m, 2H), 7.24 (d, J=5.5 Hz, 2H), 8.61 (d, J=5.5 Hz, 2H).

β-Lactam 1o.

Following the general procedure, 1.0 g (2.8 mmol) was treated with BBLS for 24 h to give 0.35 g (1.11 mmol, 35%) of (+)-1o, 0.11 g (0.35 mmol, 12%) of 2o and 0.13 g (0.41 mmol, 15%) of 2o-trans.

1o: mp 156–160° C.; $[\alpha]_{578}^{25}$=+48° (c=1.0, $CHCl_3$); >95% ee; $^1$H NMR (300 MHZ, $CDCl_3$) δ (ppm): 1.74 (s, 3H), 3.76 (s, 3H), 5.45 (d, J=5.1 Hz, 1H), 6.00 (d, J=5.1 Hz, 1H), 6.83 (d, J=8.9 Hz, 2H), 7.23 (d, J=8.9 Hz, 2H), 7.50 (d, J=9.2 Hz, 2H), 8.23 (d, J=9.2 Hz, 2H);

2o: mp 158–159° C.; $[\alpha]_{578}^{25}$=−52° (c=1.0, MeOH); >95% ee; $^1$H NMR (500 MHZ, $CDCl_3$) δ (ppm): 2.37 (m, 1H), 3.76 (s, 3H), 5.31 (m, 1H), 5.35 (d, J=5.0 Hz, 1H), 6.38 (d, J=9.1 Hz, 2H), 7.24 (d, J=9.1 Hz, 2H), 7.52 (d, J=8.8, 2H), 8.27 (d, J=8.8, 2H);

2o-trans: mp 98–100° C.; $^1$H NMR (500 MHZ, $CDCl_3$) δ (ppm): 3.40 (d, J=6.2 Hz, 1H), 3.74 (s, 3H), 4.73 (dd, J=6.3, 1.1 Hz, 1H), 6.79 (d, J=9.3 Hz, 2H), 7.16 (d, J=9.3 Hz, 2H), 7.51 (d, J=9.3 Hz, 2H), 8.25 (d, J=9.3 Hz, 2H).

What is claimed is:

1. A process for the resolution of an enantiomeric mixture of an acyloxy substituted β-lactam, the process comprising combining the enantiomeric mixture with homogenized liver to form a reaction mixture, selectively hydrolyzing the acyloxy substituent of one of the enantiomers in the reaction mixture, and recovering β-lactam having an unhydrolyzed acyloxy substituent from the reaction mixture.

2. The process of claim 1 wherein the mixture is a racemic mixture.

3. The process of claim 2 wherein the racemic mixture comprises an ethereal solvent.

4. The process of claim 2 wherein the racemic mixture comprises toluene solvent.

5. The process of claim 1 wherein the mixture is a mixture of the 3S, 4R and the 3R, 4S enantiomers.

6. The process of claim 5 wherein the mixture is a racemic mixture.

7. The process of claim 1 wherein the homogenized liver is homogenized avian or homogenized mammalian liver.

8. The process of claim 1 wherein the homogenized liver is homogenized beef liver.

9. The process of claim 1 wherein the reaction mixture comprises homogenized beef liver.

10. The process of claim 1 wherein the β-lactam has the formula:

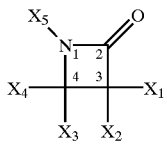

wherein $X_1$ is —$OX_6$;

$X_2$ is hydrogen, hydrocarbyl, substituted hydrocarbyl, or heterocyclo;

$X_3$ is hydrogen, hydrocarbyl, substituted hydrocarbyl, or heterocyclo;

$X_4$ is hydrocarbyl, substituted hydrocarbyl, or heterocyclo;

$X_5$ is hydrogen, hydrocarbyl, substituted hydrocarbyl, —$COX_{10}$, —$COOX_{10}$, or —$CONX_8X_{10}$;

$X_6$ is acyl;

$X_8$ is hydrogen, hydrocarbyl, substituted hydrocarbyl, or heterocyclo; and $X_{10}$ is hydrocarbyl, substituted hydrocarbyl, or heterocyclo.

11. The process of claim 10 wherein $X_2$ and $X_3$ are hydrogen.

12. The process of claim 10 wherein $X_2$ and $X_3$ are hydrogen, $X_5$ is hydrogen, hydrocarbyl, substituted hydrocarbyl, —$COX_{10}$, or —$COOX_{10}$, and $X_{10}$ is as defined in claim 10.

13. The process of claim 10 wherein $X_5$ is hydrogen, hydrocarbyl, substituted hydrocarbyl, —$COX_{10}$, or —$COOX_{10}$, and $X_{10}$ is as defined in claim 10.

14. The process of claim 10 wherein $X_2$ is hydrogen, $X_3$ is hydrogen, and $X_4$ is heterocyclo.

15. The process of claim 10 wherein $X_2$ is hydrogen, $X_3$ is hydrogen and $X_4$ is furyl.

16. The process of claim 15 wherein the homogenized liver is homogenized avian or homogenized mammalian liver.

17. The process of claim 15 wherein the homogenized liver is a refined fraction of homogenized avian or homogenized mammalian liver.

18. The process of claim 10 wherein the homogenized liver is homogenized avian or homogenized mammalian liver.

19. The process of claim 10 wherein the homogenized liver is a refined fraction of homogenized avian or homogenized mammalian liver.

20. The process of claim 10 wherein the homogenized liver is homogenized beef liver.

21. The process of claim 20 wherein $X_4$ is heterocyclo.

22. The process of claim 10 wherein $X_2$ and $X_3$ are hydrogen and the mixture contains the 3S, 4R and 3R, 4S enantiomers.

23. The process of claim 22 wherein the mixture is a racemic mixture of the 3S, 4R and 3R, 4S enantiomers.

24. The process of claim 23 wherein the homogenized liver is homogenized avian or homogenized mammalian liver.

25. The process of claim 23 wherein the homogenized liver is homogenized beef liver.

26. The process of claim 10 wherein $X_2$ and $X_3$ are hydrogen, $X_5$ is hydrogen, hydrocarbyl, substituted hydrocarbyl, —$COX_{10}$, or —$COOX_{10}$, $X_{10}$ is alkyl, aryl or heterocyclo and the mixture contains the 3S, 4R and 3R, 4S enantiomers.

27. The process of claim 26 wherein the mixture is a racemic mixture of the 3S, 4R and 3R, 4S enantiomers.

28. The process of claim 27 wherein the homogenized liver is homogenized avian or homogenized mammalian liver.

29. The process of claim 27 wherein the homogenized liver is homogenized beef liver.

30. The process of claim 10 wherein X2 and $X_3$ are hydrogen, $X_5$ is hydrogen, hydrocarbyl, substituted hydrocarbyl, —$COX_{10}$, or —$COOX_{10}$; $X_{10}$ is alkyl, aryl or heterocyclo; $X_4$ is 2-furyl, 3-furyl, 2-pyridyl, 3-pyridyl, 4-pyridyl, 2-thienyl, 3-thienyl, substituted phenyl, cycloalkyl, or alkenyl and the mixture contains the 3S, 4R and 3R, 4S enantiomers.

31. The process of claim 30 wherein the mixture is a racemic mixture of the 3S, 4R and 3R, 4S enantiomers.

32. The process of claim 31 wherein the homogenized liver is homogenized avian or homogenized mammalian liver.

33. The process of claim 31 wherein the homogenized liver is homogenized beef liver.

34. The process of claim 10 wherein $X_2$ and $X_3$ are hydrogen and the reaction mixture comprises the 3S, 4R and 3R, 4S enantiomers.

35. The process of claim 10 wherein $X_2$ and $X_3$ are hydrogen, $X_5$ is hydrogen, hydrocarbyl, substituted hydrocarbyl, —$COX_{10}$, or —$COOX_{10}$, $X_{10}$ is alkyl, aryl or heterocyclo and the reaction mixture comprises the 3S, 4R and 3R, 4S enantiomers.

36. The process of claim 35 wherein the homogenized liver is homogenized beef liver.

37. The process of claim 10 wherein $X_2$ and $X_3$ are hydrogen, $X_5$ is hydrogen, hydrocarbyl, substituted hydrocarbyl, —$COX_{10}$, or —$COOX_{10}$; $X_{10}$ is alkyl, aryl or heterocyclo; $X_4$ is 2-furyl, 3-furyl, 2-pyridyl, 3-pyridyl, 4-pyridyl, 2-thienyl, 3-thienyl, substituted phenyl, cycloalkyl, or alkenyl and the reaction mixture comprises the 3S, 4R, and 3R, 4S enantiomers.

38. The process of claim 37 wherein the homogenized liver is homogenized beef liver.

* * * * *

UNITED STATES PATENT AND TRADEMARK OFFICE
CERTIFICATE OF CORRECTION

PATENT NO. : 6,548,293 B1
DATED : April 15, 2003
INVENTOR(S) : Robert A. Holton et al.

It is certified that error appears in the above-identified patent and that said Letters Patent is hereby corrected as shown below:

Column 10,
Line 60, "recovering β-lactam" should read -- recovering a β-lactam --.

Column 11,
Lines 9-10, 52-54 and 58-60, claims 9, 17 and 19 should have been canceled.

Column 12,
Line 26, "wherein X2" should read -- wherein $X_2$ --.

Signed and Sealed this

Nineteenth Day of April, 2005

JON W. DUDAS
*Director of the United States Patent and Trademark Office*